United States Patent [19]

Moloney

[11] Patent Number: 5,792,922
[45] Date of Patent: Aug. 11, 1998

[54] OIL-BODY PROTEIN CIS-ELEMENTS AS REGULATORY SIGNALS

[75] Inventor: Maurice M. Moloney, Calgary, Canada

[73] Assignee: Sembiosys Genetics Inc., Calgary, Canada

[21] Appl. No.: 313,098

[22] PCT Filed: Apr. 2, 1993

[86] PCT No.: PCT/CA93/00141

§ 371 Date: Jan. 27, 1995

§ 102(e) Date: Jan. 27, 1995

[87] PCT Pub. No.: WO93/20216

PCT Pub. Date: Oct. 14, 1993

Related U.S. Application Data

[63] Continuation-in-part of Ser. No. 862,355, Apr. 2, 1992, abandoned.

[30] Foreign Application Priority Data

Apr. 15, 1992 [WO] WIPO ............... PCT/CA92/00161

[51] Int. Cl.⁶ ............... C12N 5/00; C12N 15/00; C07H 21/04
[52] U.S. Cl. ............... 800/205; 800/250; 800/255; 800/DIG. 17; 800/DIG. 69; 800/DIG. 70; 435/172.3; 435/320.1; 536/24.1; 935/6; 935/35; 935/64
[58] Field of Search ............... 435/172.1, 172.3, 435/240.04, 320.1; 536/23.1, 23.4, 23.6, 24.1, 24.5; 800/205, 250, 255, DIG. 15, 17, 69, 70; 935/6, 35, 64

[56] References Cited

FOREIGN PATENT DOCUMENTS

| 0255378 | 2/1988 | European Pat. Off. |
| WO 93/10240 | 5/1993 | WIPO |

OTHER PUBLICATIONS

JP Watson et al (1987) Molecular Biology of the Gene pp. 703–707.
Barton et al., *Plant Physiol.* (1987) 85:1103–1109.
Batchelder et al., *J. Exp.Bot. Suppl. Meeting* (Apr. 1991) 42:47; Abst. P8.58.
Bevan, *Nucl. Acid Research* (1984) 12:8711–8721.
Bowman-Vance et al., *J. Biol. Chem.* (1987) 262:11275–11279.
Bowman-Vance et al., *J. Biol. Chem.* (1988) 263:1476–1481.
Bustos et al., *EMBO J.* (1991) 10:1469–1479.
Bustos et al., *Plant Cell* (1989) 1:839–853.
Chen et al., *EMBO J* (1988) 7:297–302.
De Clerq et al., *Plant Physiol.* (1990) 94:970–979.
Fluhr et al., *Science* (1986) 232:1106–1112.
Haseloff et al., *Nature* (1988) 334:585–591.
Hatzopoulos et al., *Plant Cell* (1990) 2:457–467.
Holbrook et al., *Plant Physiology* (1991) 97:1051–1058.
Izant et al., *Cell* (1984) 36:1007–1015.
Larkins et al., *J. Cell Biochem. Suppl.* 0(9 Part C) (1985):264.
Lee et al., *Proc. Natl. Acad. Sci. USA* (1991) 88:6181–6185.
Lee et al., *Plant Physiol.* (1991) 96:1395–1397.
Marcotte et al., *Plant Cell* (1989) 1:969–976.
Moreau et al., *Plant Physiol.* (1980) 65:1176–1180.
Murphy et al., *Biochimica et Biophysica Acta* (1991) 86–94.
Murphy et al., *Biochem. J.* (1989) 258:285–293.
Murphy et al., *Biol. Chemistry Hoppe–Seyler* (1991) 372:Abst. 537.
Napoli et al., *Plant Cell* (1990) 2:279–289.
Perez-Grau et al., *Plant Cell* (1989) 1:1095–1109.
Qu et al., *Biochem. J.* (1986) 235:57–65.
Qu et al., *Biochemistry & Molecular Biology* (1990) 265:2238–2243.
Radke et al., *Theor. Appl. Genet.* (1988) 75:685–694.
Sengupta-Gopalan, *PNAS USA* (1985) 82:3320–3324.
Taylor et al., *Planta* (1990) 181:18–26.
Vandekerckhove et al., *Bio/Technology* (1989) 7:929–932.
Vasil. I.K., *Bio/Technology* (1990) 8:296–300.
Vilardell et al., *Plant Molecular Biology* (1991) 17:985–993.
Williamson et al., *Plant Physiol.* (1989) 90:1570–1576.
Yamaguchi-Shinozaki et al., *Plant Molecular Biology* (1990) 15:905–912.
K Weising et al (1988) Ann Rev Genet 22: 421–477.
L Holbrook et al (1988) Canbiocon 1988 Biotechnol Res Appl pp. 33–42.
R Qu et al (1986) Biochem J 235: 57–65.
R Qu et al (1990) J Biol Chem 265: 2238–2243.
E Herman (1987) Planta 172: 336–345.

*Primary Examiner*—Bruce R. Campell
*Attorney, Agent, or Firm*—Bereskin & Parr

[57] ABSTRACT

DNA constructs comprising 5' untranslated sequences from genes active from the late globular stage through to embryo maturity are provided. These constructs may be used to obtain expression of a DNA sequence of interest during phases of embryogenesis which precede the accumulation of storage proteins.

37 Claims, 7 Drawing Sheets

```
-867 CCATGGCTATACCCAACCTCGGTCTTGGTCACACCAGGAACTCTCTGGTAAGCTAGCTCCACTGCCCAGAAACAACCGGCCCAAATTGC
     NcoI                  31
-777 CGGAATTGCTGACCTGAGAGACGGAACATCATCGTCCGGGTCCTTGGGCGATTGCGGGAAGATGGGTCAGCTTGGGCTTGAGGACGAGAC
-687 CCGAATCGAGTCTGTTGAAAGGTTGTTCATTGGGATTTGTATACGGAGATTGGTCGTCGAGAGGTTTGAGGGAAAGGACAAATGGGTTTG
                                                                       R1
-597 GCTCTGGAGAAAGAGAGTGCGGCTTTAGAGAGAGAATTGAGAGAGATGCGGGCGATGACGGGAGGAGAGACGAGAGG
              R2                     R1
-507 ACCTGCATTATCAAAGCAGTGACGTGACGTGGTGAAATTTGGAACTTTTAAGAGGCAGATAGATTTATTATTTGTATCCATTTTCTCATTGTTC
                                   R2
-417 TAGAATGTCGGGAACAAATTTTAAAACTAAATCCTAAATTTTCTAATTTTGTTGCCAATAGTGGATATGTGGGCCGTATAGAAGGAAT
-327 CTATTGAAGGCCCAAACCCATGACGAGCCAAAGGTTCGTTTTGCGTTTTATGTTTCGGTTGCGATGCCAACGCCACATTCTGAGCTA
                          T
-237 GGCAAAAAACAAACGTGTCTCTTTGAATAGACTCCTCGTTAACACATGCAGCGGGCTGACGCCATTAACACGTGGCCTACAATT
                               I                                  M  A  D  T  A  R  G  T  H  H  D
-147 GCATGATGTCCATTGACGACTGACTTCTCGTCTCCTTTCTAATATATCTAACAACAAAAAAATGGCGGATACAGCTAGAGGAACCCATCACGAT
-57  TTTTTGATCAATCTCTCATTCAAATCTCATTCTCTCTCAGTAAACAAGAACAAAAAAAATGGCGGATACAGCTAGAGGAACCCATCACGAT
      I  I  G  R  D  Q  Y  P  M  M  G  R  D  R  D  Q  Y  Q  M  S  G  R  G  S  D  Y  S  K  S  R
34   ATCATCGGGCAGAGACCAGTACCCGATGATGGGCCGAGACCGAGACCAGTACCAGATGTCCGGACGAGGATCTGACTACTCCAAGTCTAGG
```

FIG. 2A-1

```
        Q  I  A  K  A  K  A  T  A  V  T  A  G  G  S  L  L  V  L  S  S  L  T  L  V  G  T  V  I  A  L
124  CAGATTGCTAAAGCTAAAGCTACAACTGCAACTGTCACAGCTGGTGGTTCCCTCCTTGTTCTCTCCAGCCTTACCCTTGTTGGAACTGTCATAGCTTTG

T  V  A  T  P  L  L  V  I  F  S  P  I  L  V  P  A  L  I  T  V  A  L  L  I  T  G  F  L  S
214  ACTGTTGCAACACCTCTGCTCGTTATCTTCAGCCCAATCCTTGTCCCGGCTCTCATCACAGTTGCACTCCTCATCACCGGTTTTCTTTCC

S  G  G  F  G  I  A  A  I  T  V  F  S  W  I  Y  K       ·  ·
304  TCTGGAGGGTTTGGCATTGCCGCTATAACCGTTTTCTCTTGGATTTACAAgtagcacacatttatcatcttacttcataattttgtca 394  atatgtgcatgtgttgagccagtagctttggatcaattttttggtcgaataacaaatgtaacaaattcagg 484  gaacatttggttaactaaatacgaaatttgacctagctagcttgaatgtctgtatatcatctataggtaaaatgcttggtatga Y  A  T  G  E  H  P  Q  G  S  D  K  L  D  S  A  R  M  K  L  G  S  K
574  taccttattgattgtgaatagGTACGCAACGGGAGAGCACCCACAGGATCAGACAAGTTGGACAGTGCAAGGATGAAGTTGGGAAGCAAA A  Q  D  L  K  D  R  A  Q  Y  Y  G  Q  H  T  G  G  E  H  D  R  D  T  R  G  G  Q  H
664  GCTCAGGATCTGAAAGACAGAGCTCAGTACTACGGACAACATACTGGTTGGGAACATGACCGTGACCGTACTCGTGGTGGCCAGCAC I  T  *
754  ACTACTTAAGTTACCCCACTGATGTCATCGTCATAGTCCAATGTCGGGGAGTTAGTTTATGAGGAATAAAGTGTTTAGAAT
                                                                                         KpnI
844  TTGATCAGGGGAGATAATAAAAGCCGAGTTTGAATCTTTTGTTATAAGTAATGTTTATGTGTTTCTATATGTTGTCAAATGGTACC
```

FIG. 2A-2

OIL-BODY PROTEIN CIS-ELEMENTS AS REGULATORY SIGNALS

The present application is a continuation-in-part of application Ser. No. 07/862,355 on Apr. 2, 1992, now abandoned.

TECHNICAL FIELD

This invention relates to upstream DNA sequences and their use to control expression of genes in developing plant seeds and their use.

BACKGROUND

Studies in plant gene expression have yielded a number of general conclusions concerning the elements that control expression. Plants, like other organisms both prokaryotic and eukaryotic, contain conserved or consensus sequences upstream (5') of the transcriptional start site of genes which appear capable of regulating transcriptional rates. In eukaryotes, these sequences include a motif found typically about 25 bp 5' to the transcriptional initiation site which has the sequence TATAA/TAA/T and is referred to as a TATA box. The role of this TATA box appears to be to define the transcriptional start for RNA polymerase II. A second upstream sequence is referred to as a CAAT box. Typically, this is found about 75 bases upstream of the transcriptional start and is associated with regulating the frequency of transcriptional initiation. In plants the consensus sequence may be either CCAAT or sometimes AGGA. However, neither of these alternative consensus sequences need be present in all plant genes. These sequence motifs and their DNA context within 70–90 bases upstream of the transcriptional start are often referred to as promoters. In general, 5' of the promoter region and most frequently within 2000 bases of it are cis-acting elements which confer a variety of properties on the promoter and which can modulate transcriptional activity in either a constitutive or a non-constitutive manner. These cis-acting sequences may be referred to as enhancers (if they are responsible for increases in transcription) or silencers (if they are responsible for decreases or suppression of transcription). Enhancers and silencers are frequently the sites at which nuclear proteins bind or interact. The modulating nuclear proteins are called trans-acting factors. They are considered to be very important for non-constitutive or regulated expression as they may be the major determinant of the activity of a gene in a particular tissue or organ or in response to an external stimulus. The relationship between this protein binding and the enhancer/silencer element may determine the transcriptional activity. The isolation of genes which are activated by heat, light or chemicals such as endogenous hormones or are activated in specific organs such as seeds, leaves or flowers has permitted analysis of factors which may determine how expression is regulated. In numerous, but not all, cases, it has been shown that the construction of chimeric genes which contain the promoter and optionally cis-elements from a given regulated gene and a coding sequence of a reporter protein not normally associated with that promoter gives rise to regulated expression of the reporter. The use of promoters from seed-specific genes for the expression of sequences in seed of genes that are either not normally expressed in a seed-specific manner or those that require an altered pattern of expression has been attempted on only a few occasions. In all cases to date, chimeric genes designed for seed-specific expression have used seed-storage protein regulatory signals and promoters. However, it is evident from work on storage protein gene expression that expression commences at a fairly late stage in embryogenesis, namely once the embryo has reached (in the case of dicots) the classical torpedo shape. Thus, although storage proteins express at high levels and their regulation is often transcriptional, the timing and level of expression may not be ideal for all seed-specific applications. It is, therefore, of interest to identify other seed-specific promoters and enhancers with temporal or cellular specificity different from that of seed storage proteins, such as those from oleosins.

Relevant Literature

The following disclose organ or tissue-specific regulatory sequences used to produce tissue- or organ-specific expression in transformed plants. There are several by now "classical" examples of regulated gene expression in non-seed protein chloramphenicol acetyl transferase could be expressed in a light-regulated and organ-specific manner in transgenic plants if the coding sequence for the reporter protein was fused with the promoter and upstream sequences from a pea gene encoding ribulose bisphosphate carboxylase (Fluhr, Science (1986), 232:1106–1112).

Sengupta-Gopalan et al. Proc. Natl. Acad. Sci. USA, (1985) 82:3320–3324 reported expression of a major storage protein of french beans, called β-phaseolin, in tobacco plants. The gene expressed correctly in the seeds and only at very low levels elsewhere in the plant. However, the constructs used by Sengupta-Gopalan were not chimeric. The entire β-phaseolin gene including the native 5'-flanking sequences were used. Subsequent experiments with other species (Radke et al. (1988) Theor. App. Genet. 75:685–694) or other genes (Perez-Grau, L., Goldberg, R.B., 1989, Plant Cell, 1:1095–1109) showed the fidelity of expression in a seed-specific manner in both Arabidopsis and Brassica. Radke et al. (1988), vide supra, used a "tagged" gene i.e., one containing the entire napin gene plus a non-translated "tag".

In tissue and organ specific expression there have been several examples showing that sequences upstream of the transcriptional start may be used to confer tissue/organ specificity to a gene introduced into plants by genetic engineering. Examples include engineering seed-specific gene regulation (Radke et al. (1988) vide supra; Bustos et al. (1989), Plant Cell, 1:839–853). In both examples, sequences upstream of the coding sequences of seed proteins were linked to a reporter tag (either as RNA or protein) and seed specificity was conferred on expression of the reporter. These were all storage protein genes rather than oleosins. Seed storage proteins have different temporal expression patterns from oleosins.

The DNA motifs that might give rise to seed-specific expression are now the subject of many studies. Marcotte et al. (Marcotte, W. R., Russel, I. S., Quantrano, R. S., 1989, Plant Cell, 1:969–976) studied the Em gene of wheat and proposed two motifs called "Em-boxes" which might be consensus sequences for seed-specific expression. Interestingly, one of these boxes called EM-2 is similar to that found in other storage protein genes from monocots (triticin-wheat) and even dicots (β-conglycinin-soybean). Hatzopoulos et al. (1990, Plant Cell, 2:457–467) investigated the sequences directing embryo-specific expression of a carrot lipid-body protein gene. A number of AT rich motifs were identified, being protected from digestion during DNAse treatment presumably by trans-acting proteins. The motifs identified, however, were not shown to be consensus motifs for other seed-specific genes.

DeClercq et al. Plant Physiol., (1990), 94:970–979 used the promoter of the Arabidopsis 2S albumin and combined coding sequences from both the Arabidopsis and Brazil nut 2S albumins. Fusions were made in regions showing low conservation. Transformation of both tobacco and *Brassica napus* yielded seed-specific expression and correct accumulation of the modified storage proteins. Levels of expression were between 0.05% and 0.3% of total cellular protein.

Another example of this form of seed-specific expression of foreign sequences was the expression of leu-enkephalins in seeds. To obtain seed specific expression, a chimeric DNA sequence encoding a 2S albumin and a short oligonucleotide encoding leu-enkephalin (a pentapeptide) was included in the albumin coding sequences between the 6th and 7th cysteines of the native protein (Vanderkerhove et al. Bio/Technology, (1989) 7:929–932). Again this gene expressed in a seed-specific manner allowing the accumulation of up to 50 nmol leu-enkaphalin per g of seed.

Genomic clones encoding oil-body proteins with their associated upstream regions have been reported for two species, maize (*Zea mays*, Bowman-Vance and Huang, (1987) J. Biol. Chem., 262:11275–11279; and Qu and Huang, (1990) J. Biol. Chem., 265:2238–2243) and carrot (Hatzopoulos et al. (1990) Plant Cell, 2:457–467). cDNAs and genomic clones have also been reported for one cultivated oilseed, *Brassica napus* (Murphy, et al. (1991), Biochem. Biophys. Acta, 1088:86–94; and Lee and Huang (1991) Plant Physico 96:1395–1397.) Reports on the expression of these oil-body protein genes in developing seeds have varied. In the case of *Zea mays*, transcription of genes encoding oil-body protein isoforms began quite early in seed development and were easily detected 18 days after pollination. In non-endospermic seeds such as the dicotyledonous plant *Brassica napus* (Canola), expression of oil-body protein genes seems to occur much later in seed development (Murphy, et al. (1989), Biochem. J., 258:285–293) than with corn.

SUMMARY OF THE INVENTION

Methods and compositions are described for the exploitation of an oil-body protein transcriptional regulatory sequence and optionally its accompanying 5' untranslated leader sequence for the expression of heterologous genes in a seed-specific manner. The method includes the steps of transforming a plant cell with a DNA construct comprising the regulatory sequence and a DNA sequence other than the open reading frame native to the regulatory sequence, generating a plant from the transformed cell and growing it under conditions whereby seed is produced and the DNA sequence is expressed under the transcriptional control of the regulatory region. These sequences will be valuable in applications where expression of a seed-borne product needs to be modified, enhanced or suppressed. They could also be used to produce modified seeds containing foreign proteins to increase the intrinsic value of the seed.

BRIEF DESCRIPTION OF THE DRAWINGS

FIG. 2A SEQ ID NO:1 shows the DNA sequence of an Arabidopsis genomic clone encoding a 18 KDa oil-body protein. The open reading frame is interrupted by a short intron (which is marked) and the two exons are translated and indicated in IUPAC single letter amino-acid codes.

BRIEF DESCRIPTION OF THE SPECIFIC EMBODIMENTS

Figure 1:
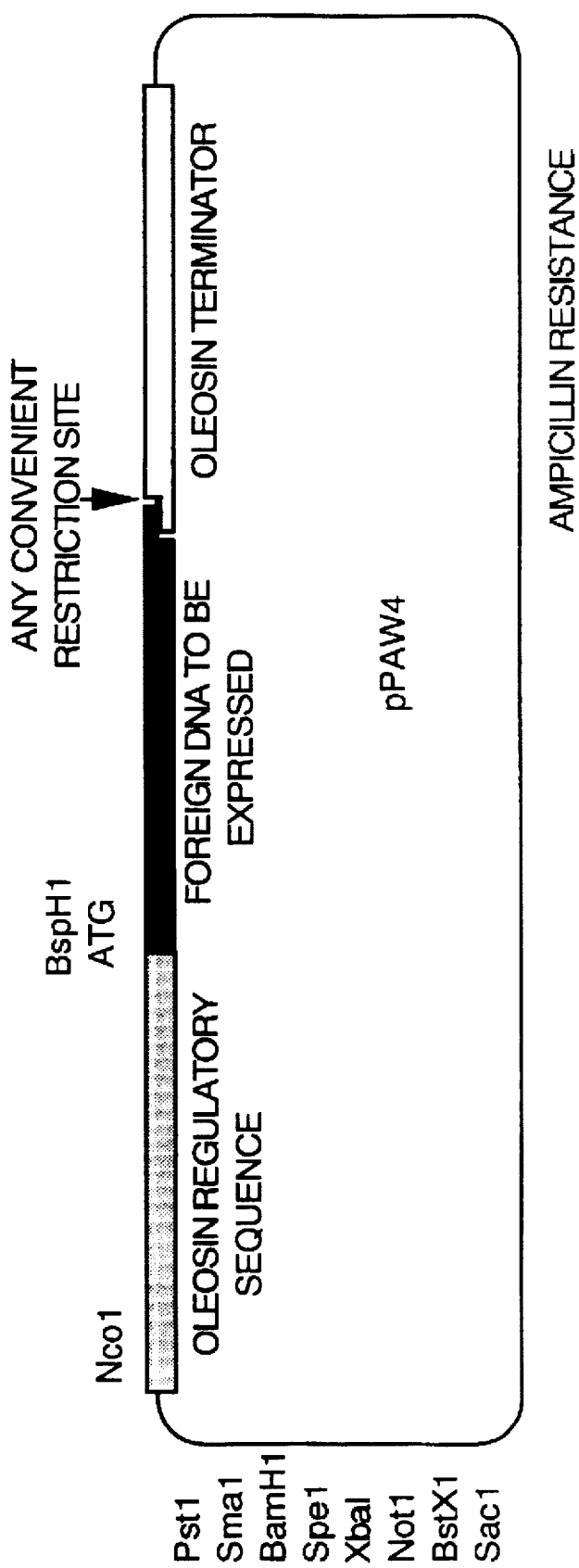
FIG. 1 shows a schematic diagram of vector pPAW4 enclosing an oleosin regulatory sequence, an initiation codon, foreign DNA to be expressed, an oleosin terminator sequence and an ampicillin resistance gene.

In accordance with the subject invention, DNA constructs are provided which allow for modulation of plant phenotype in seed, particularly during early phases of embryogenesis. The DNA constructs provide for regulation of transcription in seed, using 5' untranslated sequences from genes active from the late globular stage through to embryo maturity (cotyledonary stage). Downstream from and under transcriptional initiation regulation of an oil body protein gene initiation region will be a DNA sequence of interest which will be prepared which allow for integration of the transcription cassette into the genome of a plant cell. Conveniently, a multiple cloning site downstream from the seed specific transcriptional initiation region may be included so that the integration construct may be employed for a variety of DNA sequences in an efficient manner.

Of particular interest is a regulatory sequence from an oil body protein gene, preferably an oil body protein gene expressed in dicotyledonous oil seeds. It has been reported that oil-body proteins accumulate considerably later than either oils (triacylglycerides) or storage proteins. This later expression would limit the value of any promoters associated with these genes for seed-specific expression as they could not be used for modification of expression of genes during early phases of embryogenesis. Surprisingly, however, expression of these genes in dicotyledonous oil-seeds was found to occur much earlier than had hitherto been believed. Thus, the promoters and upstream elements of these genes are valuable for a variety of uses involving the modification of metabolism during phases of embryogenesis which precede the accumulation of storage proteins.

Oil-body proteins have been identified in a wide range of taxonomically diverse species (see, for example, Moreau et al. Plant Physiol. (1980), 65:1176–1180; Qu et al. Biochem. J., (1986) 235:57–65). These proteins are uniquely localized in oil-bodies and are not found in organelles of vegetative tissues. In *Brassica napus* (rapeseed) there are at least three polypeptides associated with the oil-bodies of developing seeds (Taylor et al. (1990), Planta, 181:18–26). The numbers and sizes of oil-body associated proteins may vary from species to species. In corn, for example, there are four immunologically distinct polypeptides found in oil-bodies (Bowman-Vance and Huang, 1988, J. Biol. Chem., 263:1476–1481). Oleosins have been shown to comprise regions of alternate hydrophilicity, hydrophobicity and hydrophilicity (Bowman-Vance and Huang, 1987, J. Biol. Chem., 262:11275–11279). The amino acid sequences of oleosins from corn, rapeseed and carrot have been obtained. See Qu and Huang, 1990, J. Biol. Chem., 265:2238–2243, Hatzopoulos et al. 1990, Plant Cell, 2:457–467, respectively. In an oilseed such as rapeseed, oleosin may comprise between 8% (Taylor et al. 1990, Planta, 181:18–26) and 20% (Murphy et al. 1989, Biochem. J., 258:285–293) of total seed protein. Such a level is comparable to that found for many seed storage proteins.

Of particular interest is a transcriptional initiation region associated with early embryogenesis, particularly the period preceding expression of storage proteins, so that in the early development of seed, it provides the desired level of transcription of the DNA sequence of interest. Normal plant embryogenesis typically goes through a series of defined phases. For dicotyledonous seeds, embryogenesis includes the following phases: globular stage, heart stage, torpedo stage, and cotyledonary stage. For the purposes of this application, the definition of these terms is provided by Ray, Steves, and Fultz in Botany, (Saunders College Publishing), Chapter 17, page 294. Normally, the transcriptional initiation region will be obtainable from a gene which is expressed in the early formation of seed. Desirably the transcriptional initiation region maintains its activity from the late globular through cotyledonary stage, more desirably continues active from the globular stage through the heart, torpedo and cotyledonary stages of embryogenesis. By obtainable is intended a transcriptional initiation region having a nucleotide sequence sufficiently similar to that of a natural oil body protein gene transcriptional initiation region sequence to provide for transcription in the early formation of seed. The sequence may be naturally occurring, synthetic or partially synthetic.

The transcriptional initiation region from the oil body protein generally will be provided in a cassette which will include in the 5'-3' direction of transcription, a transcriptional initiation region, a DNA sequence of interest and a transcriptional termination region, wherein the transcriptional regulatory regions are operably joined and functional in plant cells. One or more introns may also be present. After each manipulation, a DNA to be used in the final construct may be restricted and operably joined to other DNA to be used in the final construct, where each of the partial constructs may be cloned in the same or different plasmids. In a preferred embodiment, a coding sequence with a compatible restriction site may be ligated at the position corresponding to codon #1 of the oil-body protein gene. A schematic diagram of this substitution is shown in FIG. 1. The recombinant coding sequence may be inserted in such a way that it completely replaces the coding sequence of the oil-body protein gene and is thus flanked at its 3' end by the oil-body protein gene terminator and polyadenylation signal. Alternatively, polymerase chain reaction amplification may be carried out to produce DNA fragments containing the transcriptional initiation region conveniently flanked by restriction sites. The amplified fragments can be joined to the coding sequence for a polypeptide of interest, in a transcriptional or translational fusion, for example, to produce a chimeric gene in which the coding sequence of the polypeptide of interest is transcribed under the control of the transcription initiation region on the PCR amplified fragment.

The transcriptional initiation region may be native to or homologous to the host cell, or foreign or heterologous to the host cell. By foreign is intended that the transcriptional initiation region is not found in the wild-type host into which the construct comprising the transcriptional initiation region is inserted. Generally, the regulatory sequence comprises DNA of up to 1.5 Kb 5' of the translational start of an oil-body protein gene. This sequence may be modified at the position corresponding to the first codon of the desired protein by site-directed mutagenesis (Kunkel TA, 1985, Proc. Natl. Acad. Sci. USA, 82:488–492) or by introduction of a convenient linker oligonucleotide by ligation if a suitable restriction site is found near the N-terminal codon.

In some cases it will be desirable to express the DNA sequence of interest as a fusion protein, particularly as a fusion protein with the oil body protein. The DNA sequence of interest can be inserted by routine techniques into the oil body protein coding sequence, in frame with the oil body protein coding sequence, such that transcription of the chimeric gene will produce a fusion protein. The fusion protein will preferably contain the coding region for amino acids number 44 through 122 in the Arabidopsis oil body protein as shown in FIG. 2A (SEQ.ID.NO.:1), or the equivalent region from an oil body protein of a species other than Arabidopsis, to provide for transport to the oil body in cases where this is desirable.

In order to isolate oil body protein coding sequences from other species, at least two approaches may be used. The first is to use the Arabidopsis clone described in the Examples as a probe in genomic libraries of other plant species. This clone will hybridize well with oleosin clones from closely related species, in particular, essentially all cruciferous plants. For species which are evolutionarily divergent from Arabidopsis, for example, solanaceae, leguminaceae and all monocotyledons, an alternative method involves the use of an antibody raised against the gene product of an oleosin clone such as the Arabidopsis clone. This antibody may be used to screen a seed-derived cDNA expression library, for example using lambda gt11; Huynh et al. (1985) in cDNA Cloning, Vol. 1, A Practical Approach, Ed. Grover IRL Press, pp. 49–78. This approach yields a cDNA clone of the oleosin for the new species which may then be used to isolate the genomic clone from a genomic library of that species by standard DNA hybridization techniques.

The DNA sequence of interest may be any open reading frame encoding a peptide of interest, for example, an enzyme, or a sequence complementary to a genomic sequence, where the genomic sequence may be at least one of an open reading frame, an intron, a non-coding leader sequence, or any other sequence where the complementary sequence will inhibit transcription, messenger RNA processing, for example splicing or translation. The DNA sequence of interest may be synthetic, naturally derived or a combination thereof. Depending upon the nature of the DNA sequence of interest, it may be desirable to synthesize the sequence with plant preferred codons. The plant preferred codons may be determined from the codons of highest frequency in the proteins expressed in the largest amount in the particular plant species of interest.

The DNA sequence of interest may encode any of a variety of recombinant proteins. Examples of recombinant proteins which might be expressed by this procedure include anticoagulants, such as Hirudin, lymphokines such as those of the interleukin family, peptide hormones such as gonadotrophin releasing hormone, immunological reagents such as multi or single-chain antibodies and a variety of industrial valuable enzymes such as proteases, lipases and polyglucan hydrolases.

The termination region which is employed will be primarily one of convenience, since the termination regions appear to be relatively interchangeable. The termination region may be native with the DNA sequence of interest, or may be derived from another source. Convenient termination regions are available and include the 3' end of the oil body protein gene terminator and polyadenylation signal from the same gene from which the 5' regulatory region is obtained. Alternatively, a different terminator and polyadenylation signal may be employed with similar results, for example, the terminator of the nopaline synthase gene of Agrobacterium.

The expression cassette may additionally contain a means for identifying transformed cells and/or selecting for transformed cells. For example the recombinant gene may be linked with a constitutively expressed selectable marker such as a gene for antibiotic resistance or herbicide resistance or a screenable marker, such as a gene conferring bioluminescence or colored properties to transformed cells.

The DNA sequence of interest flanked at its 5' end by the oil-body protein promoter and regulatory sequences and at its 3' end by a terminator may be introduced into a suitable transformation vector including Agrobacterium Ti or binary plasmids, or a simple cloning plasmid (e.g., pUC19, pBR322) for use in direct DNA uptake to plant cells via microinjection, electroporation, PEG-mediated uptake or a biolistic method. These methods are well known to those skilled in the art of plant transformation. See, for example, Horsch et al. (1985), Science, 227:1229–1231; Newhaus and Spangenberg (1990), Physiol. Plant, 79:213–217; and Sandford et al. (1990), Physiol. Plant, 79:206 –209.

Transformed plants may be obtained from the transformed cells using standard regeneration protocols (see for example: Moloney et al. (1989), Plant Cell Rep., 8:238–242) compatible with the transformation method.

The expression cassette, constructed as described above, expresses essentially preferentially in developing seeds. The plant cells which have been transformed with an appropriate fusion peptide therefore are grown into plants in accordance with conventional ways and allowed to set seed. See, for example, McCormick et al., Plant Cell Rep. (1986) 5:81–84. Two or more generations may be grown and either pollinated with the same transformed strain or different strains, identifying the resulting hybrid having the desired phenotypic characteristic, to ensure that the subject phenotypic characteristic is stably maintained and inherited and then seeds harvested for isolation of the peptide of interest or for use to provide seeds with the new phenotypic property. The regenerated plants are then cultivated identically to non-recombinant plants in growth chambers, greenhouses or in the field and will show seed-specific expression of the recombinant gene at the mRNA level and often at the level of polypeptide or protein.

It is possible that the polypeptide/protein will itself be valuable and could be extracted and, if desired, further purified. Alternatively the polypeptide/protein or even the mRNA itself may be used to confer a new biochemical phenotype upon the developing seed. New phenotypes could include such modifications as altered seed-protein or seed oil composition, enhanced production of pre-existing desirable products or properties and the reduction or even suppression of an undesirable gene product using antisense, ribozyme or co-suppression technologies (Izant and Weintraub (1984), Cell 36: 1007–1015, antisense; Hazelhoff and Gerlach (1988), Nature 334:585–591, ribozyme; Napoli, et al. (1990), Plant Cell, 2:279–289, co-suppression).

If the transformation has been performed to produce a new seed protein or peptide which requires extraction, this can be done using aqueous extraction with or without low concentrations of detergents, such as non-denaturing amounts of sodium dodecyl sulphate (SDS), Triton-X-100, Tween 20, MEGA-8 or any other detergent known not to irreversibly inactivate the desired protein. To extract the protein or polypeptide, dry seeds are ground by hand or in a mechanical grinder to produce an aqueous slurry or suspension. This can be resolved into three phases (particulate, aqueous soluble, and hydrophobic) by centrifugation, such as at 50,000×g. Depending upon the nature of the product, it may be further purified in each of these phases and after solublization, may be selectively precipitated by the use of ammonium sulfate or purified using column chromatography, for example, using ion exchange, gel filtrates or affinity matrices.

While the ideal host for the regulatory sequence reported here would be a cruciferous plant, it is possible to use these promoters in a wide variety of plant species given the relatively high conservation oleosin of genes. The major barrier to the use of these promoters is between monocotyledonous and dicotyledonous species. For transformations involving this specific expression on a monocot, a monocot olesin regulatory sequence should be used. For dicot seed-specific expression, a dicot oleosin regulatory sequence should be employed. The reported sequence can be used in a wide variety of dicotyledonous plants, including all members of the Brassica genus and crucifers in general. Solanaceous plants, such as tobacco and tomato, also recognize the sequences and show correct regulation of expression in developing seeds.

It is expected that the desired proteins would be expressed in all embryonic tissue, although different cellular expression can be detected in different tissues of the embryonic axis and cotyledons. This invention has a variety of uses which include improving the intrinsic value of plant seeds by their accumulation of altered polypeptides or novel recombinant peptides or by the incorporation or elimination of a metabolic step. In its simplest embodiment, use of this invention may result in improved protein quality (for example, increased concentrations of essential or rare amino acids), improved liquid quality by a modification of fatty acid composition, or improved or elevated carbohydrate composition. Examples include the expression of sulfur-rich proteins, such as those found in lupins or brazil nuts in a seed deficient in sulphurous amino acid residues. Alternatively, a fatty acyl coenzyme A (COA) a transferase enzyme capable of modifying fatty acid ratios in triglycerides (storage lipid) could be expressed. In cases where a recombinant protein is allowed to accumulate in the seed, the protein could also be a peptide which has pharmaceutical, industrial or nutritional value. In this case, the peptide could be extracted from the seed and used in crude or purified form, as appropriate for the intended use. The protein could be one truly foreign to the plant kingdom, such as an animal hormone, enzyme, lymphokine, anticoagulant, or the like could be expressed in seed. The heterologous protein could then be extracted from the seeds and used for experimental, nutritional or pharmaceutical purposes after partial or complete purification.

The following examples are offered by way of illustration and not by limitation.

EXAMPLES

Example 1

The oil body protein gene from Arabidopsis was isolated on a 15 kb insert present in a clone from an *Arabidopsis thaliana* v. Columbia genomic library in page λ EMBL3A by hybridization to a *B. napus* oleosin clone. A 1.8 kb fragment containing approximately 868 base pairs 5' of the oleosin protein translational start was subcloned into a plasmid vector. The Arabidopsis 18 KDa oleosin gene is conveniently cloned as a 1803 bp fragment flanked by Nco1 and Kpn1 sites in a vector called pPAW4 (see FIG. 1). In order to convert the fragment into an expression cassette for general use with a variety of foreign/alternative genes, two modifications must be made. Firstly, using the technique of site-directed mutagenesis (Kunkel, supra) mutations at positions −2, −1 and +4 are introduced using a mis-matched oligonucleotide. The mutations required are A to T (−2), A to C (−1) and G to A (+4). These mutations have the effect of creating a BspH1 site at positions −2 to +4. The BspH1 site (T/CATGA) encloses the ATG initiation codon and gives a recessed end compatible with an Nco1 cut. A second modification involves digestion with EcoRV and Msc1 which releases a 658 bp fragment containing most of the coding sequence of the native oleosin. This leaves blunt ends at the cut sites which on separation of the vector and an ancillary sequence from the EcoRV-Msc1 fragment, permits recircularization of the vector-promoter-terminator combination. This recircularization is performed in the presence of an oligonucleotide linker containing restriction sites not found in the original 1803 Kb fragment.

On recircularization, a plasmid containing all the upstream sequences of the oleosin gene, a transcriptional start site and an initiation codon embedded in a BspH1 site is obtained. Thirty-one bases downstream of this is a short polylinker containing one or more unique restriction sites. To introduce any DNA sequence into this cassette the foreign sequence should have, or should be modified to contain, a BspH1 or Nco1 site at the initial ATG position. For sequences to be expressed as proteins this will assure conservation of the distance between the "cap" site and the initiator codon.

The DNA sequence to be inserted should terminate with a cohesive end of a restriction site not found on the plasmid. The polylinker interposed into the expression cassette may be chosen with this site in mind. Digesting the plasmid with BspH1 and the appropriate restriction enzyme for the 3' end of the foreign sequence will ensure that a directional cloning of the desired DNA fragment may be effected. Using appropriate ligation conditions, the plasmid expression cassette with BspH1 and a site compatible with the desired DNA fragment are incubated together to produce a ligated product as shown in FIG. 1.

The complete construct from Nco1-Kpn1 is now excised and introduced into an appropriate plant transformation vector such as an Agrobacterium plasmid. In order to introduce the construct into common Agrobacterium plasmids such as Bin 19 (Bevan, Nucl. Acid Research (1984) 12:8711–8721) it may be necessary to use one of the additional restriction sites in plasmid pPAW4. In one scenario the plasmid could be cut with Sma1 and Kpn1. The resulting purified fragment then is ligated to a Kpn1 oligonucleotide linker and digested withy Kpn1. This provides a non-directional Kpn1 fragment for introduction into Bin 19. Alternatively, the construct may be excised with Kpn1 and BamH1 and ligated directionally into pBIN 19 previously cut with the same restriction enzymes. The resulting Agrobacterium binary plasmid is mobilized into a disarmed Agrobacterium strain by tripartite mating (Ditta, et al. (1980), PNAS 77: 7347–7351) or DNA transformation of competent Agrobactertium (An, (1988), Plant Mol. Biology Manual, A31–19, Kluwer Academic, Dordrecht, Netherlands).

The Agrobacterium harboring the recombinant Bin 19 is used to transform any susceptible plant, e.g., Brassica sp. by standard explant co-cultivation (Horsch et al. (1985), supra). The transformed cells are selected in culture with kanamycin using the co-transferred antibiotic resistance genes (neomycin phosphotransferase) also contained between the T-DNA borders of pBin 19. These transformed cells are induced to regenerate whole plants by standard procedures (e.g. for an oilseed such as rapeseed. See, Moloney et al. Plant Cell Rep., (1989), 8: 238–242). The regenerated plants are permitted to flower and are self-fertilized (or may be cross-fertilized). In cases where the foreign DNA in the construct encodes a translatable product, this product may be isolated from aqueous extractions of the mature seed and subsequent fractionation of the slurry by centrifugation (30 min at 100.000×g). Depending on the desired product it may partition with any one of the three phases obtained. It may be localized in the pellet, aqueous soluble phase or in the lipid film on the surface of the centrifuged sample.

Alternatively, it may not be necessary to extract the product as the purpose of the expression may be to divert metabolism in the seed thus changing the phenotype of the seed (e.g. by altering size or colour of the seed, changing the ratio of fatty acid residues in the seed or interdicting a particular metabolic step considered to render the seed less useful or valuable. Such metabolic steps might include the production of antinutritional secondary products which reduce the value or desirability of the seed when present. In such cases, the seed, per se, is simply harvested and used in accordance with usual procedures.

Example 2

A number of constructs containing varying amounts of the DNA sequence from the 5' transcriptional initiation region of the Arabidopsis oleosin gene joined operably to the coding region for β-glucuronidase (GUS) were prepared using PCR. The constructs are designated according to the amount of the oleosin 5' region contained, for example, the 2500 construct has approximately 2500 base pairs of the oleosin 5' region. The constructs were introduced into *Brassica napus* and tobacco and the expression of the β-glucuronidase gene was measured as described in detail below. The GUS expression results of five constructs, the 2500, the 1200, the 800, the 600 and the 200 constructs in transformed *Brassica napus* plants are shown in Table I. A negative control (untransformed plant) is also shown. The GUS expression results of two constructs, the 2500 and the 800 constructs, in transformed tobacco plants are shown in Table II. Table III shows the developmental timing of the expression of the oleosin promoter in transgenic embryos.

The constructs were made using standard molecular biology techniques, including restriction enzyme digestion, ligation and polymerase chain reaction (PCR). As an illustration of the techniques employed, the construction of the 800 construct is described in detail.

In order to obtain a DNA fragment containing approximately 800 base pairs from the 5' transcriptional initiation region of the Arabidopsis oleosin gene in a configuration suitable for ligation to a GUS coding sequence, a PCR based approach was used. This involves the use of the polymerase chain reaction to amplify the precise sequence desired for the expression analysis. To perform the necessary PCR amplification, two oligonucleotide primers were synthesized (Milligen-Biosearch, Cyclone DNA synthesizer) having the following sequences:

```
                                       Pst 1 oleosin seq
5' primer: (SEQ ID NO:3)  5'CACTGCAGGAACTCTCTGGTAA 3'
(GVR10)
```

The italicized bases correspond to nucleotide positions −833 to −817 in the sequence reported in FIG. 2A SEQ.ID.NO:1 The additional nucleotides 5' of this sequence in the primer are not identical to the oleosin gene, but were included in order to place a Pst1 site at the 5' end of the amplification product. The Pst1 site is underlined.

A second (3') primer was synthesized which had the following sequence:

```
3' primer (ALP 1) (SEQ ID NO:4)
              BamH1      oleosin seq
5-CTACCCGGGATCCTGTTTACTAGAGAGAATG-3
              Sma1
```

This primer contains the precise complement (shown in italics) to the sequence reported in FIG. 2A SEQ.ID.NO:1 from base −13 to −30. In addition, it contains a further 13 bases at the 5' end. This sequence is not complementary to the oleosin gene, but was added to provide two (overlapping) restriction sites, Sma1 and BamH1, at the 3' end of the amplification product to facilitate cloning of the PCR fragment.

These two primers were used in a PCR amplification reaction to produce DNA fragment containing the sequence between nucleotides −833 and −13 of the oleosin gene with a Pst1 site at the 5' end and Sma1 and BamH1 sites at the 3' end. PCR amplification was performed using the enzyme Taq polymerase (Perkin-Elmer-Cetus) using the conditions recommended by the enzyme manufacturer and a temperature program of 92° C. (denaturation) 1 min, 55° C. (annealing) 1 min and 72° C. (elongation) 1 min. The template was the oleosin genomic clone shown in FIG. 2B, top panel, which in the original λ library isolate contained approximately 15 kilobases of Arabidopsis DNA.

Figure 2B:
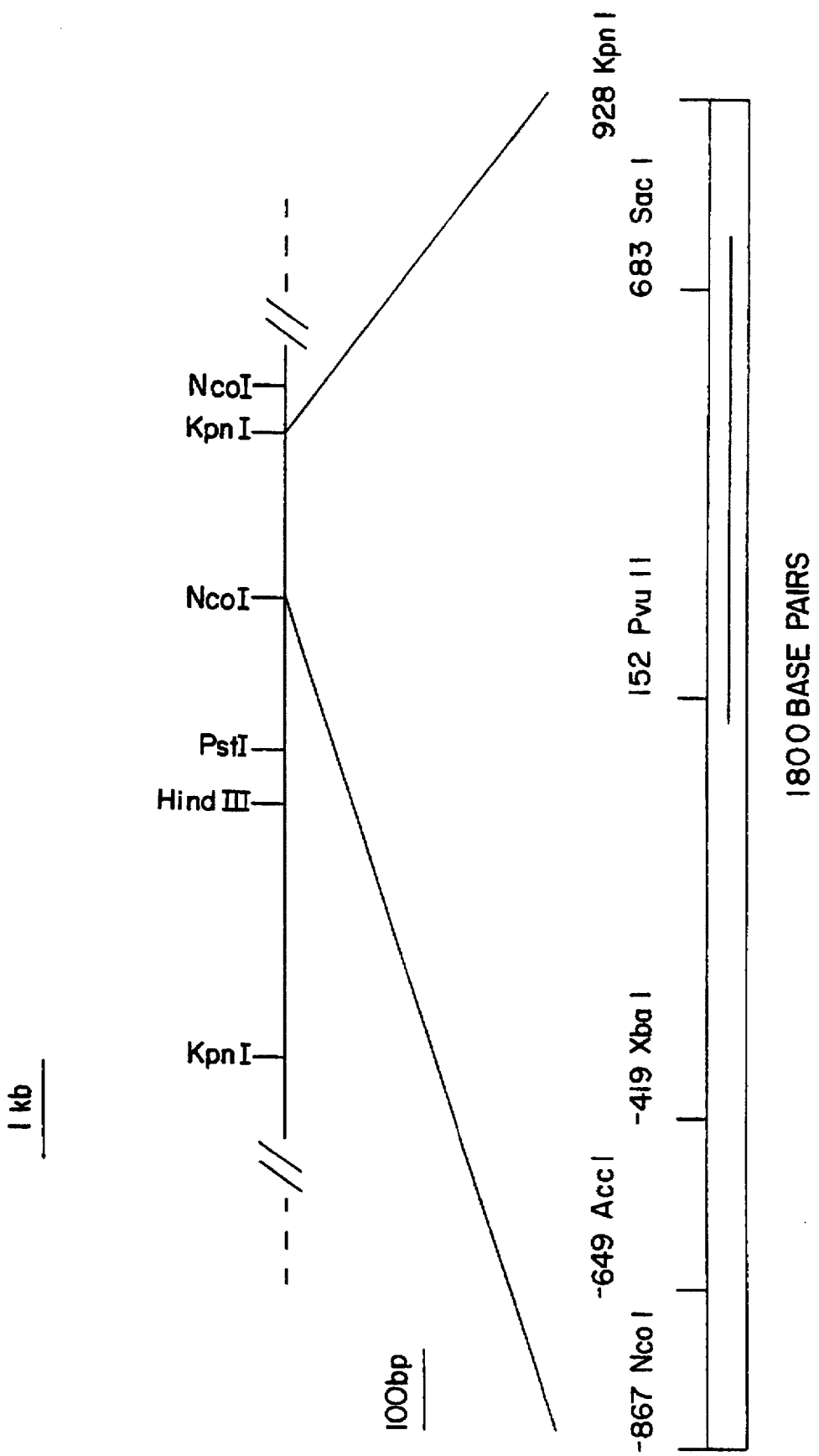
FIG. 2B shows the restriction fragment from an Agrobacterium EMBL3 genomic library which encloses the Arabidopsis 18 KDa oil-body protein coding sequence. The approximate position of the coding region is highlighted.
Figure 3A:
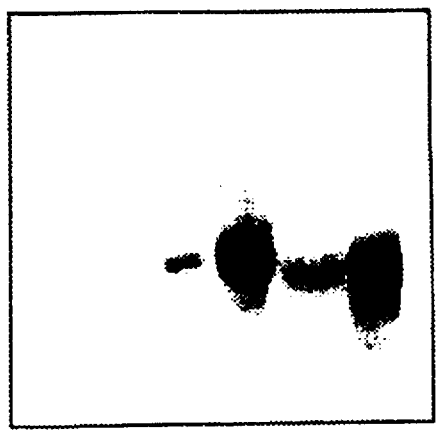
FIGS. 3A–3C show the effects of 10μM ABA on the developmental expression of oleosin mRNA using a Northern blot analysis of total RNA. A) (70 μg per lane) using 50 ng$^{32}$P dCTP labelled OB990 as a probe (spec. act. $10^9$ dpm/μg DNA). Heart-(H):(13-day), torpedo-(T) (17-day), and cotyledonary-(C) (21–25 day) stage microspore-derived embryos with (+) and without (−) treatment for 48 h with 10 μM ABA. The blot was exposed to Kodak XAR5 film at 70° C. for 20 minutes. The apparent size difference of the mRNAs in the different lanes is due to interfering quantities of starch in the different mRNA preparations. All the lanes were equally loaded as judged by OD260 measurements and EtBr-staining. B) A 4.5 hour exposure of FIG. 3-A C) Relative intensity of the mRNA accumulation as determined by scanning densitometry.
Figure 3B:
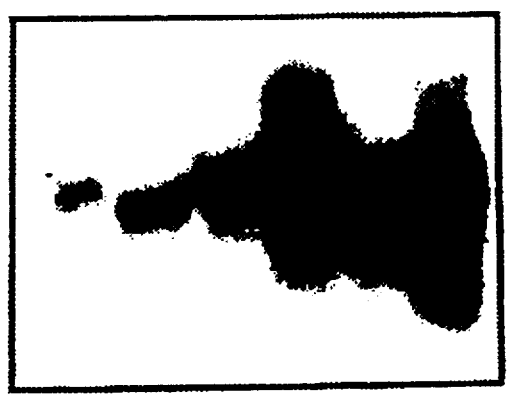
Figure 3C:
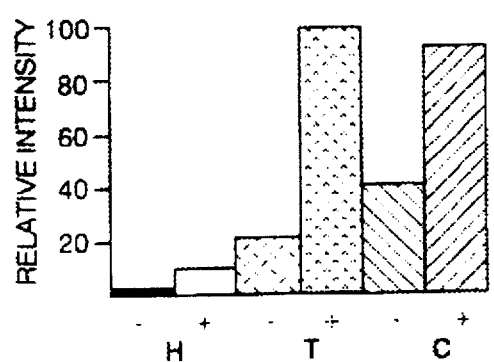
Figure 4:
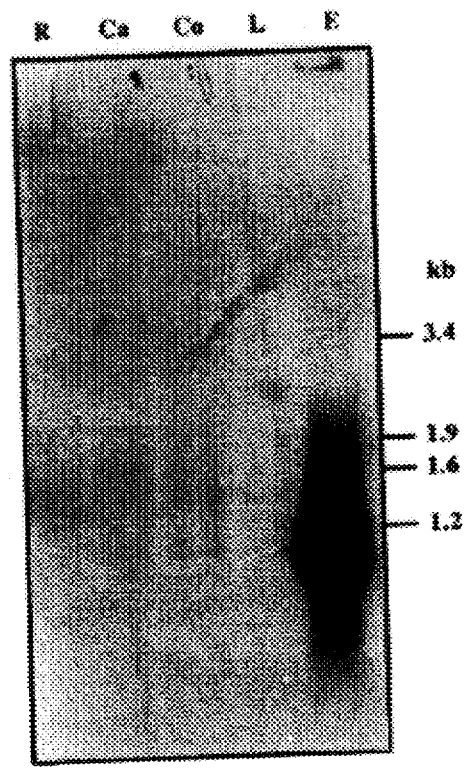
FIG. 4 shows the tissue specificity of oleosin. 50 μg of poly (A)+ RNA of roots (R), callus (Ca), Cotyledons (Co), leaves (L), and 24-day post-anthesis zygotic embryos (E) was probed with 50 ng of $^{32}$P dCTP labelled OB990 (spec. act. $10^8$ dpm/μg DNA).
Figure 5:
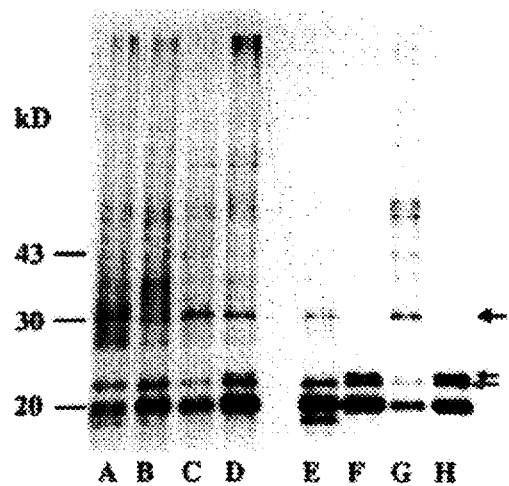
FIG. 5 shows the developmental sensitivity of oil body protein synthesis to applied ABA. An estimated 10,000 dpm were loaded per well for paired samples of controls (lanes A,C,E,G) and ABA-treated (lanes B,D,F,H). All samples were treated for 2d with ABA, then labeled for 4 h with 1.85 MBq/mL [$^{355}$] methionine. Lanes A and B, 10-d-old cultures, sieved on 62 μm screens to obtain globular embryos. Lanes C and D, 13-d-old cultures sieved on 125 μm screens to obtain heart stage embryos. Lanes E and F, 17-d-old cultures, sieved on 250 μm screens to obtain torpedo to early cotyledonary embryos. Lanes G and H, 25-d-old cultures, sieved on 500μm screens to obtain cotyledonary stage embryos.

The amplification product (OLEO p800) was gel purified on 0.7% agarose, recovered using the glass bead method of Vogelstein and Gillespie (Preparative and analytical purification of DNA from agarose. Proc. Natl. Acad. Sci. USA 1979 76:615–619) and digested with Pst1. The digestion product was gel purified and end filled using DNA polymerase Klenow fragment then cut with Sma1 to produce a blunt ended fragment. This was cloned into the Sma1 site of pUC19 to yield the plasmid pUC OLEOp800. Using the asymmetric positioning of the Acc1 site in the insert (at the position corresponding to −649 in the oleosin gene as shown in FIG. 2B) it was possible to select both orientations of insertion into pUC vector. The clone having the insert oriented such that the 5' most end of the amplified fragment (in the direction of transcription) is proximal to the unique Hind III site in the puC19 cloning vector and the 3' most end of the amplified fragment is proximal to the unique Eco RI site in the pUC19 closing vector.

The resulting plasmid was then cut with BamH1 to yield the fragment OLEOp800 flanked by BamH1 sites. This fragment, BamH1-OLE0800, was cloned into the BamH1 sites of a BamH1 digested plasmid designated Hsp-GUS1559. HspGUS1559 is a plasmid used as a binary vector in Agrobacteriwn, derived from the vector pCGN 1559 (MacBride and Summerfeldt, 1990, Plant Molecular Biology, 14, 269–276) with an insert containing heat shock promoter (flanked by BamH1 sites), the β-glucuronidase open reading frame and a nopaline synthase terminator (derived from pB1221, Jefferson RA in Cloning Vectors 1988, Eds. Pouwels P., Enger-Valk BE, Brammer WJ., Elsevier Science Pub BV, Amsterdam section VII, Ai11). BamH1 digestion of HspGUS1559 results in the release of the heat shock promoter and permits the insertion of any other BamH1 fragment in its place. The BamH1-OLEOp800 fragment was ligated into this site to yield the Agrobacternium pOLEOp800GUS1559. This plasmid was used to transform E. coli and the amplified plasmid was introduced into Agrobacterium (strain EHA101) by electroporation as described above (Rogers et al., 1988, Plant Molecular Biology Manual, A2: 1–12, Eds. Gelvin S. and Schilperoort, R. Kluwer Academic, Dordrecht, Netherlands).

The resultant Agrobacterium strain (EHA 101× pOLEOp800GUS1559) was used to transform Brassica napus plants by the method of Moloney et al. (Moloney, M. M., Walker, J. M., Sharma, K. K. (1989) Plant Cell Reports 8:238–242) or tobacco plants by the method of Horsch et al.(Horsch et al. Science (1985) 227:1299–1302). The resultant transgenic plants were allowed to set seed, and GUS expression assays (Jefferson R. A. (1987), Plant Mol. Biol. Rep. 5 387–405) were performed on the developing seeds and also on non-reproductive plant parts as controls. GUS expression reported is an average obtained from approximately five seeds from each of approximately five different transgenic plants.

The other constructs were prepared by the same PCR method described above using the appropriate primers for amplifying the −2500 fragment, the −1200 fragment, the −600 fragment or the −200 fragment. The results in Brassica napus expressed as specific activity of GUS enzyme are shown in Table I. The results in tobacco are shown in Table II.

These results demonstrate that the oleosin fragment from −833 to −813 used in the 800 construct contains sufficient information to direct seed-specific expression of a reporter gene in transgenic Brassica napus embryos as early as heart stage and that the Arabidopsis oleosin promoter is capable of directing transcription in plants other than Arabidopsis. These experiments also show that the sequences present in this promoter construct contain the cis elements required for an increase in transcription in response to the addition of abscisic acid, a characteristic of the native oleosin promoter.

It should be noted that the seed-specific expression demonstrated here does not depend on interactions with the native terminator of an oleosin gene 3' end. In this example, the 3' oleosin terminator was replaced by a terminator derived from the nopaline synthase gene of Agrobacterium. Thus, the sequence in the 800 construct is sufficient to drive the desired expression profile independent of ancillary sequences.

TABLE I

Seed Specific Expression in *Brassica napus*
GUS Activity (in pmol product/min/mg protein)

| Promoter/GUS Construct | Seed (Torpedo Stage) +ABA* | −ABA | Root | Leaf | Stem | Seed (Late-Cotyledonary) |
|---|---|---|---|---|---|---|
| 2500 | 10,185 | 7,709 | 444 | 46.9 | 88.2 | 11,607 |
| 1200 | 18,298 | 1,795 | | | | 8,980 |
| 800 | 2,250 | 475 | 285 | 277 | 650 | 7,130 |
| 600 | 1,506 | 144 | | | | 1,365 |
| 200 | 18.1 | 64.8 | 260 | 5.9 | 26 | 11 |
| Negative Control-Non-transformed Plant | 18.4 | 13.9 | 300 | 6.1 | 30 | 14 |

*ABA is treatment for 24 hours with $10^{-5}$M abscisic acid prior to GUS activity measurement

TABLE II

Seed Specific Expression in Tobacco

| Promoter/GUS Constructs | GUS Activity (in pmol product/min/mg protein) Mature Seeds |
|---|---|
| 2500 | 11,330 |
| 800 | 10,970 |

TABLE III

Developmental Expression in *Brassica napus*
GUS ACTIVITY (in pmol product/min/mg protein)

| Promoter/ GUS Construct | Heart Stage | Torpedo Stage | Early Cotyledonary Stage | Mid-Cotyledonary Stage | Late Cotyledonary Stage |
|---|---|---|---|---|---|
| 2500 | 272 | 1207 | 2541 | 1819 | 11,607 |
| 1200 | 124 | 262 | 388 | 5094 | 8,980 |
| 800 | 149 | 260 | 962 | 2617 | 7,128 |
| 600 | 59 | 41 | 29 | 38 | 1,365 |
| 200 | 30 | 25 | 15 | 20 | 11 |
| Negative Control | | | 11 | 14 | 14 |

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of expressing a DNA sequence of interest in a seed cell, said method comprising:

growing a plant capable of developing seed, wherein said plant comprises cells containing integrated into their genome an expression cassette comprising in the 5'–3' direction of transcription as operably linked components, a transcriptional regulatory region obtained from an oil body protein gene, a DNA sequence of interest heterologous to said regulatory region, and a transcriptional termination region, under conditions whereby seed is produced in which said DNA sequence is expressed under transcriptional control of said regulatory region and during a phase of embryogensesis which precedes accumulation of storage proteins.

2. The method according to claim 1 wherein said DNA sequence is expressed from the formation of a globular embryo through to early cotyledonary stage.

3. The method according to claim 1, wherein said oil body protein gene is from a dicotyledenous plant.

4. The method according to claim 1, wherein said phase is selected from the group consisting of globular, heart, torpedo and early cotyledonary stage.

5. The method according to claim 1, wherein said plant is a dicotyledonous plant.

6. The method according to claim 1, wherein said plant is from the genus Brassica.

7. A DNA construct comprising:

a chimeric gene comprising a transcriptional regulatory region obtained from an Arabidopsis oil body protein gene fused to a DNA sequence of interest heterologous to said regulatory region.

8. The DNA construct according to claim 7, wherein said tanscriptional regulatory region comprises the sequence shown in SEQ.ID.NO:1 from nucleotide 1 to nucleotide 867.

9. An expression casette comparing:

as operably linked components, a transcriptional regulatory region obtained from Arabidopsis oil body protein gene, a DNA sequence of interest heterologous to said regulatory region, and a transcriptional termination region.

10. An isolated transcriptional regulatory region comprising a DNA molecule comprising the sequence shown in SEQ.ID.NO:1 from nucleotide 1 to nucleotide 867.

11. A plant comprising:

cells containing integrated into their genome, a chimeric gene comprising a transcriptional regulatory region obtained from an Arabidopisis oil body protein gene, wherein said transcriptional regulatory region is fused to a DNA sequence of interest heterologous to said regulatory region.

12. Seed comprising:

cells containing integrated into their genome, a chimeric gene comprising a transcriptional regulatory region obtainable from an Arabidopsis oil body protein gene, wherein said transcriptional regulatory region is fused to a DNA sequence of interest heterologous to said regulatory region.

13. Seed according to claim 12, wherein said transcriptional regulatory region comprises the sequence shown in SEQ.ID.NO:1 from nucleotide 1 to nucleotide 867.

14. Seed according to claim 12, wherein said seed is dicotyledonous.

15. Seed according to claim 13, wherein said seed in an oilseed.

16. A method for altering seed-specific metabolism, said method comprising:

growing a plant capable of developing seed, wherein said plant comprises cells containing integrated into their genome an expression cassette comprising in the 5'–3' direction of transcription, a transcriptional initiation region obtained from an oil body protein gene, a DNA sequence of interest other than a sequence native to said initiation region, and a transcriptional termination region, under conditions whereby seed is produced in which said DNA sequence is expressed under transcriptional control of said transcriptional initiation region wherein expression of said DNA sequence altars seed-specific metabolism during a phase of embroyogenesis which precedes accumulation of storage proteins.

17. The method according to claim 16, wherein said altering is reducing or suppressing expression of en dogenous genes expressed in plant seeds.

18. The method according to claim 16, wherein said transcriptional initiation region includes a silencer element.

19. The method according to claim 16, wherein a transcribed strand of said DNA sequence is complementary to mRNA endogenous to said cells.

20. A method for producing heterologous polypeptide in seed, said method comprising:

growing a plant capable of developing seed, wherein said plant comprises cells containing integrated into their genome an expression cassette comprising in the 5'–3' direction of transcription, a transcriptional initiation region obtained from an oil body protein gene, a DNA sequence of interest encoding a polypeptide heterologous to said plant, and a transcriptional termination region, under conditions whereby seed is produced in which said DNA sequence is expressed under transcriptional control of said transcriptional initiation region and during a phase of embryogenesis which precedes accumulation of storage proteins.

21. A plant part, comprising a DNA construct according to claim 7.

22. A plant part according to claim 21, wherein said part is a leaf, stem, root, flower, fruit or seed.

23. The method according to claim 1, wherein said oil body protein gene is obtainable from the group consisting of (a) *Brassica napus;*

(b) *Zea mays;*

(c) carrot; and (d) Arabidopsis.

24. A method according to claim 1, wherein said transcriptional regulatory region is obtained from Arabidopsis.

25. A method according to claim 24, wherein said transcriptional regulatory region comprises the sequence shown in SEQ.ID.NO.:1 from nucleotide 1 to nucleotide 867.

26. An isolated transcriptional regulatory region obtained from an Arabidopsis oil body protein gene.

27. A plant according to claim 11, wherein said transcriptional regulatory region comprises the sequence shown in SEQ.ID.NO.:1 from nucleotide 1 to nucleotide 867.

28. A plant according to claim 11, wherein said plant is a dicotyledonous plant.

29. A plant according to claim 11, wherein said plant is from the genus Brassica.

30. A method according to claim 16, wherein said transcriptional initiation region is obtained from Arabidopsis.

31. A method according to claim 16, wherein said transcriptional initiation region comprises the sequence shown in SEQ.ID.NO.:1 from nucleotide 1 to nucleotide 867.

32. A method according to claim 16, wherein said plant is a dicotyledonous plant.

33. A method according to claim 16, wherein said plant is from the genus Brassica.

34. A method according to claim 20, wherein said transcriptional initiation region is obtained from Arabidopsis.

35. A method according to claim 20, wherein said transcriptional initiation region comprises the sequence shown in SEQ.ID.NO: 1 from nucleotide 1 to nucleotide 867.

36. A method according to claim 20, wherein said plant is a dicotyledonous plant.

37. A method according to claim 20, wherein said plant is from the genus Brassica.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 1800 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: exon
( B ) LOCATION: 868..1220

( i x ) FEATURE:
( A ) NAME/KEY: exon
( B ) LOCATION: 1461..1626

( i x ) FEATURE:
( A ) NAME/KEY: CDS
( B ) LOCATION: join(868..1220, 1461..1626)

( x i ) SEQUENCE DESCRIPTION: SEQ ID NO:1:

```
CCATGGCTAT ACCCAACCTC GGTCTTGGTC ACACCAGGAA CTCTCTGGTA AGCTAGCTCC      60

ACTCCCCAGA AACAACCGGC GCCAAATTGC CGGAATTGCT GACCTGAAGA CGGAACATCA     120

TCGTCGGGTC CTTGGGCGAT TGCGGCGGAA GATGGGTCAG CTTGGGCTTG AGGACGAGAC     180

CCGAATCGAG TCTGTTGAAA GGTTGTTCAT TGGGATTTGT ATACGGAGAT TGGTCGTCGA     240
```

```
GAGGTTTGAG GGAAAGGACA AATGGGTTTG GCTCTGGAGA AAGAGAGTGC GGCTTTAGAG      300

AGAGAATTGA GAGGTTTAGA GAGAGATGCG GCGGCGATGA CGGGAGGAGA GACGACGAGG      360

ACCTGCATTA TCAAAGCAGT GACGTGGTGA AATTTGGAAC TTTTAAGAGG CAGATAGATT      420

TATTATTTGT ATCCATTTTC TTCATTGTTC TAGAATGTCG CGGAACAAAT TTTAAAACTA      480

AATCCTAAAT TTTTCTAATT TTGTTGCCAA TAGTGGATAT GTGGGCCGTA TAGAAGGAAT      540

CTATTGAAGG CCCAAACCCA TACTGACGAG CCCAAAGGTT CGTTTGCGT  TTTATGTTTC      600

GGTTCGATGC CAACGCCACA TTCTGAGCTA GGCAAAAAC  AAACGTGTCT TTGAATAGAC      660

TCCTCTCGTT AACACATGCA GCGGCTGCAT GGTGACGCCA TTAACACGTG GCCTACAATT      720

GCATGATGTC TCCATTGACA CGTGACTTCT CGTCTCCTTT CTTAATATAT CTAACAAACA      780

CTCCTACCTC TTCCAAAATA TATACACATC TTTTGATCA  ATCTCTCATT CAAAATCTCA      840

TTCTCTCTAG TAAACAAGAA CAAAAAA ATG GCG GAT ACA GCT AGA GGA ACC          891
                               Met Ala Asp Thr Ala Arg Gly Thr
                                1                   5

CAT CAC GAT ATC ATC GGC AGA GAC CAG TAC CCG ATG ATG GGC CGA GAC        939
His His Asp Ile Ile Gly Arg Asp Gln Tyr Pro Met Met Gly Arg Asp
        10              15                  20

CGA GAC CAG TAC CAG ATG TCC GGA CGA GGA TCT GAC TAC TCC AAG TCT        987
Arg Asp Gln Tyr Gln Met Ser Gly Arg Gly Ser Asp Tyr Ser Lys Ser
25              30                  35                      40

AGG CAG ATT GCT AAA GCT GCA ACT GCT GTC ACA GCT GGT GGT TCC CTC       1035
Arg Gln Ile Ala Lys Ala Ala Thr Ala Val Thr Ala Gly Gly Ser Leu
                45                  50                  55

CTT GTT CTC TCC AGC CTT ACC CTT GTT GGA ACT GTC ATA GCT TTG ACT       1083
Leu Val Leu Ser Ser Leu Thr Leu Val Gly Thr Val Ile Ala Leu Thr
                60                  65                  70

GTT GCA ACA CCT CTG CTC GTT ATC TTC AGC CCA ATC CTT GTC CCG GCT       1131
Val Ala Thr Pro Leu Leu Val Ile Phe Ser Pro Ile Leu Val Pro Ala
        75                  80                  85

CTC ATC ACA GTT GCA CTC CTC ATC ACC GGT TTT CTT TCC TCT GGA GGG       1179
Leu Ile Thr Val Ala Leu Leu Ile Thr Gly Phe Leu Ser Ser Gly Gly
        90                  95                  100

TTT GGC ATT GCC GCT ATA ACC GTT TTC TCT TGG ATT TAC AAG               1221
Phe Gly Ile Ala Ala Ile Thr Val Phe Ser Trp Ile Tyr Ly
105                 110                 115

TAAGCACACA TTTATCATCT TACTTCATAA TTTTGTGCAA TATGTGCATG CATGTGTTGA     1281

GCCAGTAGCT TTGGATCAAT TTTTTGGTC  GAATAACAAA TGTAACAATA AGAAATTGCA     1341

AATTCTAGGG AACATTTGGT TAACTAAATA CGAAATTTGA CCTAGCTAGC TTGAATGTGT     1401

CTGTGTATAT CATCTATATA GGTAAAATGC TTGGTATGAT ACCTATTGAT TGTGAATAGG     1461

TAC GCA ACG GGA GAG CAC CCA CAG GGA TCA GAC AAG TTG GAC AGT GCA       1509
Tyr Ala Thr Gly Glu His Pro Gln Gly Ser Asp Lys Leu Asp Ser Ala
 1              5                   10                  15

AGG ATG AAG TTG GGA AGC AAA GCT CAG GAT CTG AAA GAC AGA GCT CAG       1557
Arg Met Lys Leu Gly Ser Lys Ala Gln Asp Leu Lys Asp Arg Ala Gln
                20                  25                  30

TAC TAC GGA CAG CAA CAT ACT GGT TGG GAA CAT GAC CGT GAC CGT ACT       1605
Tyr Tyr Gly Gln Gln His Thr Gly Trp Glu His Asp Arg Asp Arg Thr
        35                  40                  45

CGT GGT GGC CAG CAC ACT ACT TAAGTTACCC CACTGATGTC ATCGTCATAG          1656
Arg Gly Gly Gln His Thr Thr
        50              55

TCCAATAACT CCAATGTCGG GGAGTTAGTT TATGAGGAAT AAAGTGTTTA GAATTTGATC     1716

AGGGGGAGAT AATAAAAGCC GAGTTTGAAT CTTTTTGTTA TAAGTAATGT TTATGTGTGT     1776
```

TTCTATATGT TGTCAAATGG TACC                                                                    1800

( 2 ) INFORMATION FOR SEQ ID NO:2:

( i ) SEQUENCE CHARACTERISTICS:
        ( A ) LENGTH: 173 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ala | Asp | Thr | Ala | Arg | Gly | Thr | His | His | Asp | Ile | Ile | Gly | Arg | Asp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Gln | Tyr | Pro | Met | Met | Gly | Arg | Asp | Arg | Asp | Gln | Tyr | Gln | Met | Ser | Gly |
|     |     |     | 20  |     |     |     |     | 25  |     |     |     |     | 30  |     |     |
| Arg | Gly | Ser | Asp | Tyr | Ser | Lys | Ser | Arg | Gln | Ile | Ala | Lys | Ala | Ala | Thr |
|     |     | 35  |     |     |     |     | 40  |     |     |     |     | 45  |     |     |     |
| Ala | Val | Thr | Ala | Gly | Gly | Ser | Leu | Leu | Val | Leu | Ser | Ser | Leu | Thr | Leu |
|     | 50  |     |     |     |     | 55  |     |     |     |     | 60  |     |     |     |     |
| Val | Gly | Thr | Val | Ile | Ala | Leu | Thr | Val | Ala | Thr | Pro | Leu | Leu | Val | Ile |
| 65  |     |     |     |     | 70  |     |     |     |     | 75  |     |     |     |     | 80  |
| Phe | Ser | Pro | Ile | Leu | Val | Pro | Ala | Leu | Ile | Thr | Val | Ala | Leu | Leu | Ile |
|     |     |     |     | 85  |     |     |     |     | 90  |     |     |     |     | 95  |     |
| Thr | Gly | Phe | Leu | Ser | Ser | Gly | Gly | Phe | Gly | Ile | Ala | Ala | Ile | Thr | Val |
|     |     |     | 100 |     |     |     |     | 105 |     |     |     |     | 110 |     |     |
| Phe | Ser | Trp | Ile | Tyr | Lys | Tyr | Ala | Thr | Gly | Glu | His | Pro | Gln | Gly | Ser |
|     |     | 115 |     |     |     |     | 120 |     |     |     |     | 125 |     |     |     |
| Asp | Lys | Leu | Asp | Ser | Ala | Arg | Met | Lys | Leu | Gly | Ser | Lys | Ala | Gln | Asp |
|     | 130 |     |     |     |     | 135 |     |     |     |     | 140 |     |     |     |     |
| Leu | Lys | Asp | Arg | Ala | Gln | Tyr | Tyr | Gly | Gln | Gln | His | Thr | Gly | Trp | Glu |
| 145 |     |     |     |     | 150 |     |     |     |     | 155 |     |     |     |     | 160 |
| His | Asp | Arg | Asp | Arg | Thr | Arg | Gly | Gly | Gln | His | Thr | Thr |     |     |     |
|     |     |     |     | 165 |     |     |     |     | 170 |     |     |     |     |     |     |

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CACTGCAGGA ACTCTCTGGT AA                                                                      22

( 2 ) INFORMATION FOR SEQ ID NO:4:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CTACCCGGGA TCCTGTTTAC TAGAGAGAAT G                                                            31